United States Patent
Paes et al.

(10) Patent No.: US 12,036,303 B2
(45) Date of Patent: Jul. 16, 2024

(54) STABLE SKIN-LIGHTENING COSMETIC COMPOSITION

(71) Applicant: Natura Cosméticos S.A., São Paulo (BR)

(72) Inventors: Fabiana Paes, São Paulo (BR); Camila Pereira Santos, São Paulo (BR); Priscila Carollo Moncayo, São Paulo (BR); Mayara Baradel, São Paulo (BR)

(73) Assignee: NATURA COSMÉTICOS S.A., São Paulo (BR)

( * ) Notice: Subject to any disclaimer, the term of this patent is extended or adjusted under 35 U.S.C. 154(b) by 698 days.

(21) Appl. No.: 17/255,160

(22) PCT Filed: Jun. 18, 2019

(86) PCT No.: PCT/BR2019/050228
§ 371 (c)(1),
(2) Date: Dec. 22, 2020

(87) PCT Pub. No.: WO2020/000075
PCT Pub. Date: Jan. 2, 2020

(65) Prior Publication Data
US 2021/0244643 A1    Aug. 12, 2021

(30) Foreign Application Priority Data
Jun. 26, 2018 (BR) .................. 102018013183-4

(51) Int. Cl.
*A61K 8/67* (2006.01)
*A61K 8/34* (2006.01)
(Continued)

(52) U.S. Cl.
CPC ............. *A61K 8/676* (2013.01); *A61K 8/34* (2013.01); *A61K 8/345* (2013.01); *A61K 8/36* (2013.01);
(Continued)

(58) Field of Classification Search
CPC .... A61K 8/676; A61K 8/9728; A61K 8/9789; A61K 8/34; A61K 8/345; A61K 8/36; A61K 8/365; A61K 8/96; A61Q 19/02
See application file for complete search history.

(56) References Cited

U.S. PATENT DOCUMENTS 4,983,382 A * 1/1991 Wilmott .............. A61K 8/34
                                                         514/474
6,060,546 A   5/2000 Powell et al.
(Continued)

FOREIGN PATENT DOCUMENTS

BR    PI0411481 A     7/2006
WO    WO-0015221 A1 *  3/2000  ........... A61K 31/375

OTHER PUBLICATIONS

International Searching Authority, International Search Report and Written Opinion received for International Application No. PCT/BR2019/050228, dated Sep. 3, 2019, 11 pages, National Institute of Industrial Property, Brazil.

*Primary Examiner* — Blessing M Fubara
(74) *Attorney, Agent, or Firm* — Alston & Bird LLP

(57) ABSTRACT

A multi-action skin-lightening cosmetic composition is provided. The cosmetic composition comprises ascorbic acid delivered in a stable form in a high concentration and, optionally, other complementary active ingredients.

6 Claims, 1 Drawing Sheet

(51) Int. Cl.
  *A61K 8/36* (2006.01)
  *A61K 8/365* (2006.01)
  *A61K 8/96* (2006.01)
  *A61K 8/9728* (2017.01)
  *A61K 8/9789* (2017.01)
  *A61Q 19/02* (2006.01)

(52) U.S. Cl.
  CPC ............... *A61K 8/365* (2013.01); *A61K 8/96* (2013.01); *A61K 8/9728* (2017.08); *A61K 8/9789* (2017.08); *A61Q 19/02* (2013.01)

(56) References Cited

U.S. PATENT DOCUMENTS

| | | | |
|---|---|---|---|
| 6,271,295 | B1 | 8/2001 | Powell et al. |
| 7,179,841 | B2 * | 2/2007 | Zielinski ................ A61K 8/676 |
| | | | 514/474 |
| 2004/0105873 | A1 * | 6/2004 | Gupta ................... A61Q 19/00 |
| | | | 424/401 |
| 2005/0002976 | A1 | 1/2005 | Wu |
| 2008/0292560 | A1 | 11/2008 | Tamarkin et al. |

* cited by examiner

STABLE SKIN-LIGHTENING COSMETIC COMPOSITION

FIELD

The present invention relates to a multi-action skin-lightening cosmetic composition comprising ascorbic acid delivered in a stable form in a high concentration and, optionally, additional active ingredients.

BACKGROUND

Ascorbic acid, also known as vitamin C, is an antioxidant capable of fighting off free radicals and promoting skin lightening, both for normal skin, giving a lighter and brighter tone thereto, and for skin with dark spots caused by the production and excessive deposition of melanin (melasmas).

Ascorbic acid acts stains as it inhibits tyrosinase production, an enzyme that transforms tyrosine into melanin and creates pigmentation. For being water-soluble and not synthesized within the human body, it must be supplemented orally. Topically, the use of creams and serums comprising small amounts of it has been widely used for promoting a number of benefits to the skin. In addition to lightening spots, it also stimulates the production of collagen, smoothing superficial expression lines and fighting off even the deepest wrinkles.

However, ascorbic acid, in general, reacts with oxygen from water or air leading to oxidation and darkening of compositions comprising the same, especially at high concentrations, hence prejudicing its efficacy. For this reason, to maintain its stability, it has been used in pure form or given in anhydrous formulations, in dispersed form at high concentration with the consistency of fine grains that act as exfoliators on the skin, in general, in a silicone medium.

However, efficient lightening action is known to be achieved by ascorbic acid in soluble form that enables it to act in the deeper layers of the skin.

In an attempt to overcome these delivery and solubilization drawbacks, the state of the art suggests as a means of delivery and stabilization of ascorbic acid, the use of silicones or polyhydric alcohols, as well as the use of heat to favor solubilization.

The ingredient is also sensitive to temperatures greater than 40°, which limits its processing at high temperatures aiming at solubilization.

Most of the prior-art documents teaches the use of ascorbic acid as an active ingredient responsible for the effect or in complex compositions for the same purpose. It is frequently mentioned in water-in-oil compositions at very low concentrations, exercising distinct skin lightening functions, in dispersed (and not solubilized) form, being intended for uses other than cosmetic or even including specific is stabilizing ingredients (some harmful to the skin especially in the long term).

Due to the limitations in the use of ascorbic acid at the desired concentration, it has often been used in combination with other lightening ingredients, for example, ferulic acid.

Thus, there remains a need for new cosmetic compositions aimed mainly at skin lightening, which allow incorporating a high concentration of ascorbic acid and even combining it with other complementary active ingredients, while maintaining its stability.

DETAILED DESCRIPTION

Figure 1:
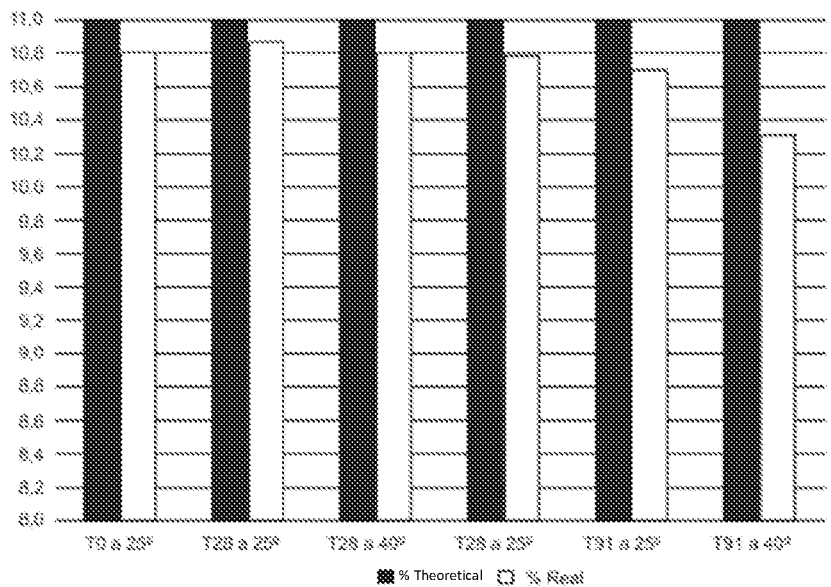
FIG. 1 shows the integrity of vitamin C (ascorbic acid) in a T91 study=valid for 24 months. In this graph, the theoretical result represents the concentration added to the formulation (first bar) and the actual result represents the concentration achieved in dosing result 9 (second bar).

The present invention deals with a stable skin-lightening cosmetic composition, which comprises a high-concentration of solubilized and stabilized ascorbic acid, particularly associated with other complementary lightening ingredients.

This desired efficiency is achieved by using a specific propylene glycol to propanediol ratio in a silicone medium, which is free of other essential complementary agents such as carbonate, providing protection against oxygen degradation at temperatures higher than 40° C., as well as an appropriate medium for solubilization and stabilization of ascorbic acid in high levels.

The stable skin-lightening cosmetic composition according to the present invention consists in particular of a multi-action lightening serum in the form of a silicone-in-glycol emulsion that allows the delivery of a high dosage of ascorbic acid, that is, greater than 5%, preferably 8 to 15%, more preferably 10% ascorbic acid, which is properly solubilized at high concentration (30 to 40%) of glycols, particularly selected from propylene glycol and propanediol.

Percentages, as expressed here, are relative to the weight of the final composition.

Adequate amounts of propylene glycol and propanediol can vary from 1.5:1 to 1:1.5, preferably 18% propylene glycol and 22% propanediol.

The stable skin-lightening cosmetic composition according to the present invention can be either anhydrous or not, that is, it can contain minor concentrations of water (up to 2%), for example, from other raw materials incorporated into the composition, without impairing the ascorbic acid stability.

In another embodiment, the present invention further contemplates a stable multi-action skin-lightening cosmetic composition, which in addition to the high concentration of ascorbic acid, further comprises other additional active ingredients that provide lightening effects, which are selected from one or more of:

from 0.01 to 1%, preferably 0.5% ferulic acid;
from 0.01 to 1%, preferably 0.35% *Schinus terebinthfolius* leaf extract (brazilian peppertree);
from 0.01 to 2%, preferably 1.5% *Candida saitoana* hydrolyzed extract;
from 0.01 to 3%, preferably 2% plankton extract;
from 0.01 to 1%, preferably 0.5% alpha-bisabolol;
from 0.01 to 6%, preferably 4% glicolic acid.

Thus, in addition to the multi-action lightening effect, the compositions according to the present invention further have antioxidant, anti-signs, anti-wrinkle, anti-spot, anti-inflammatory and/or exfoliating effects.

The following examples, without any limitation, describe the particular embodiments of the present invention.

EXAMPLES

Example 1. Skin-Lightening Cosmetic Composition According to the Present Invention The following table illustrates one embodiment of a cosmetic composition according to the present invention, which was produced by an emulsion technique known to the person skilled in the art.

TABLE 1

Cosmetic composition according to the present invention

| Ingredient | Weight based on the final composition |
| --- | --- |
| Propanediol | 22.0 |
| Propylene glycol | 18.0 |
| Caprylyl methicone, PEG-12 dimethicone/PPG-20 crosspolymer | 13.1 |
| Ascorbic acid | 11.0 |
| Dimethicone | 10.2 |
| PEG-10-dimethicone | 5.5 |
| Dimethicone-50 | 4.3 |
| Glycolic acid | 2.9 |
| Silica Dimethyl Silylate | 2.0 |
| *Plankton* extract | 1.9 |
| *Candida Saitoana* Extract | 1.4 |
| Ethoxy Diglycol | 1.0 |
| Ferulic acid | 0.5 |
| Bisabolol | 0.5 |
| *Schinus terebinthifolius* leaf extract | 0.2 |
| Perfume | 0.2 |

Example 2. Composition Stability

Stability of the composition of the present invention, according to example 1, was analyzed.

To ensure the formula's stability and shelf-life (24 months), the rules of the stability guide recommended by the Brazilian National Health Surveillance Agency—ANVISA were observed, which recommends exposing the formulation to different temperatures (5° C., 25° C. and 40° C.) for different periods of time (T0, T7, T14, T21, T28, T63, T91).

Since 25° C. and 40° C. could be more aggressive temperatures for a product with ascorbic acid, dosages were performed in the following protocol:

Time 0 (T0); Time 28 days (T28), Time 91 days (T91);
Incubator temperatures: 25° C. and 40° C.

Figure 2:
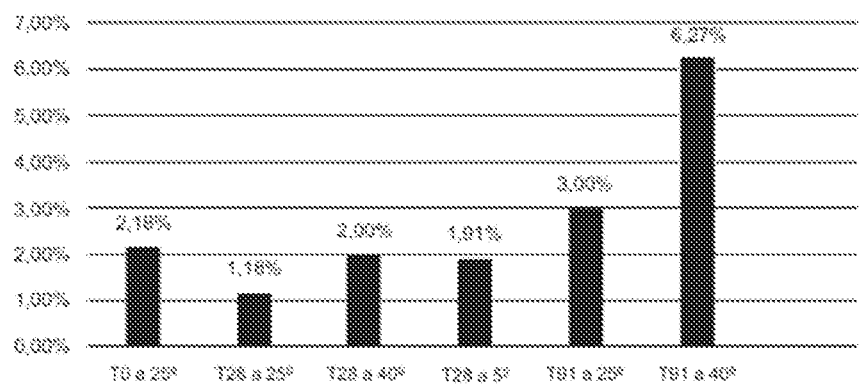
FIG. 2 shows the percentage of Vitamin C (ascorbic acid) decay in a T91 study—valid for 24 months.

For administration, a deviation error for the HPLC method of 10% below or above the % of added ascorbic acid was considered. Therefore, in FIG. 1 or 2, the drop achieved at T91 at 40° C. is highly positive as it did not reach a 10% drop.

The person skilled in the art will be able to readily assess through the teachings of the presented text and examples the advantages of the invention and to propose variations and equivalent alternatives of realization without departing from the scope of the invention as defined in the appended claims.

The invention claimed is:

1. A stable skin lightening cosmetic composition comprising at least 5% by weight solubilized and stabilized ascorbic acid in about 30% to about 40% by weight glycols; wherein the composition is in a silicone medium;
   wherein the glycols are propylene glycol and 1,3-propanediol in a weight ratio from 1.5:1 to 1:1.5.

2. The composition according to claim 1, wherein the composition comprises from about 8% to about 15% by weight ascorbic acid.

3. The composition according to claim 1, wherein the composition comprises about 10% by weight ascorbic acid.

4. The composition according to claim 1, wherein the glycols are 18% by weight propylene glycol and 22% by weight 1,3-propanediol.

5. The composition according to claim 1, further comprising one or more additional active ingredients selected from:
   from 0.01 to 1% by weight ferulic acid;
   from 0.01 to 1% by weight *Schinus terebinthfolius* leaf extract (brazilian peppertree);
   from 0.01 to 2% by weight *Candida saitoana* hydrolyzed extract;
   from 0.01 to 3% by weight plankton extract;
   from 0.01 to 1% by weight alpha-bisabolol; and
   from 0.01 to 6% by weight glycolic acid.

6. The composition according to claim 1, further comprising one or more additional active ingredients selected from:
   0.5% by weight ferulic acid;
   0.35% by weight *Schinus terebinthfolius* leaf extract (brazilian peppertree);
   1.5% by weight *Candida saitoana* hydrolyzed extract;
   2% by weight plankton extract;
   0.5% by weight alpha-bisabolol; and
   4% by weight glycolic acid.

* * * * *

UNITED STATES PATENT AND TRADEMARK OFFICE
CERTIFICATE OF CORRECTION

PATENT NO. : 12,036,303 B2
APPLICATION NO. : 17/255160
DATED : July 16, 2024
INVENTOR(S) : Fabiana Paes et al.

Page 1 of 1

It is certified that error appears in the above-identified patent and that said Letters Patent is hereby corrected as shown below:

In the Claims

In Column 4, Line 25, Claim 5, delete "*terebinthfolius*" and insert -- *terebinthifolius* --, therefor.

In Column 4, Line 36, Claim 6, delete "*terebinthfolius*" and insert -- *terebinthifolius* --, therefor.

Signed and Sealed this
Twelfth Day of November, 2024

Katherine Kelly Vidal
*Director of the United States Patent and Trademark Office*